US00PP07806P

United States Patent [19]

Fleming

[11] Patent Number: Plant 7,806

[45] Date of Patent: Feb. 25, 1992

[54] KALANCHOE PLANT NAMED PINK GLORY

[75] Inventor: Margaret M. Fleming, Soquel, Calif.

[73] Assignee: The Plant Company, Soquel, Calif.

[21] Appl. No.: 606,842

[22] Filed: Oct. 31, 1990

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Foley & Lardner

[57] ABSTRACT

A Kalanchoe plant named Pink Glory particularly characterized by its pink flower color; flower diameter of up to 17 mm at maturity; flowering response of from 9 weeks in summer to 11 weeks in winter after start of short days; very floriferous, with excellent display of many flowers; good keeping quality of both flowers and foliage; excellent free branching with or without pinching; intermediate vigor; responsive to B-9 to reduce internode length and peduncle elongation, and adaptability to pot sizes of from 10 to 15 cm and larger.

2 Drawing Sheets

The present invention relates to a new and distinctive cultivar of Kalanchoe plant, botanically known as *Kalanchoe blossfeldiana* Poelln., and referred to by the cultivar name Pink Glory.

Pink Glory, identified as 618-005, is a product of a planned breeding program which had the objective of creating new Kalanchoe cultivars for year-round commercial production having an earlier flowering response, good branching yet compact flowering plants, suitability for flowering in pots ranging from 10 to 15 cm, and having good flower and foliage keeping quality.

Pink Glory was originated from a cross made by the inventor Margaret M. Fleming in a controlled breeding program in Half Moon Bay, Calif., in 1984.

The female parent of Pink Glory was an unnamed seedling, identified as 423-001, produced from the crossing of Royalty with Cinnabar. The male parent was the cultivar identified as Sensation, disclosed in U.S. Plant Pat. No. 4,727.

Pink Glory was discovered and selected as one flowering plant within the progeny of the stated cross by Margaret M. Fleming in February of 1986 in a controlled environment in Soquel, Calif.

The first act of asexual reproduction of Pink Glory was accomplished when vegetative cuttings were taken from the initial selection in July 1986 in a controlled environment in Soquel, Calif., by Margaret M. Fleming.

Horticultural examination of controlled flowerings of successive plantings has shown that the unique combination of characteristics as herein disclosed for Pink Glory are firmly fixed and are retained through successive generations of asexual reproduction. Pink Glory has not been observed under all possible environmental conditions. The phenotype may vary significantly with variations in environment such as temperature, light intensity and daylength.

The following observations, measurements and comparisons describe plants grown in Soquel, Calif., under greenhouse conditions which approximate those generally used in commercial greenhouse practice.

The following traits have been repeatedly observed and are determined to be basic characteristics of Pink Glory which, in combination, distinguish this Kalanchoe as a new and distinct cultivar:

1. Clear pink flower color.

2. Flower diameter of 15 to 17 mm at maturity.
3. Flowering response of from an early 9 weeks in summer to 11 weeks in winter after start of short days.
4. Very floriferous, with excellent display of many flowers.
5. Excellent keeping quality of both flowers and foliage, with each floret lasting more than 2 weeks under normal conditions of finishing and holding.
6. Branches freely with or without pinching.
7. Intermediate vigor.
8. Good responsiveness to B-9 to reduce internode length and peduncle elongation.
9. Proper scheduling makes this new cultivar suitable for production in 10 cm to 15 cm and larger pots.

The accompanying colored photographic drawings show typical inflorescence and leaf characteristics of Pink Glory, with colors being as nearly true as possible with illustrations of this type.

Sheet 1 is a color photograph of Pink Glory grown as a non-pinched flowering Kalanchoe in a 10 cm pot.

Sheet 2 is a black and white photograph showing the leaves of Pink Glory at three stages of development (mature, intermediate and immature).

Of the commercial cultivars known to the inventor, the most similar to Pink Glory in flower size, color and response is the cultivar identified as Bingo, disclosed in U.S. Plant Pat. No. 5,876. However, Pink Glory is more vigorous than Bingo and has not exhibited the fasciated stems common in Bingo. The cultivar identified as Satisfaction, disclosed in U.S. Plant Pat. No. 5,894, is another commercial cultivar that may be compared to Pink Glory. Pink Glory has an earlier flowering response to short days than Satisfaction, and has larger individual flowers and total display. In addition, Pink Glory does not exhibit night closing of flowers, while night closing of the flowers of Satisfaction is a real disadvantage.

In comparison to the male parent Sensation, the flowers of Pink Glory are a clear pink, compared with the rose pink flower color of Sensation. In addition, Pink Glory flowers earlier, with Sensation blooming in approximately 11 weeks in summer and 12 or 13 weeks in winter. Pink Glory is medium in size with a fast growth rate, opposed to the more compact size of Sensation and a slower growth rate. Although the foliage of Pink Glory is larger than the foliage of Sensation, both are very durable.

As above noted, the female parent of Pink Glory is an unknown seedling 423-001, whose parents are Royalty and Cinnabar. When compared to Royalty, the flowers of Pink Glory are a more clear pink, its response is earlier (response of Royalty is 10–12 weeks), it has a larger flower diameter (flower diameter of Royalty is 12–15 mm.), it is less compact and grows faster, and is highly susceptible to foliar diseases. In comparison to Cinnabar, the flowers are a completely different color, with the flowers of Cinnabar being a bright red or red-/orange. In addition, the foliage of Pink Glory is a darker green than the foliage of Cinnabar, and somewhat more durable.

In the following description color references are made to The Royal Horticultural Society Colour Chart. The color values were determined on plant material grown as a non-pinched pot plant in a 10 cm. pot in Soquel, Calif., on Oct. 23, 1988.

Classification:

*Botanical.*—*Kalanchoe blossfeldiana* Poelln. cv. Pink Glory.

*Commercial.*—Flowering pot Kalanchoe.

Parentage:

*Female parent.*—An unnamed seedling (423-001).

*Male parent.*—Sensation; U.S. Plant Pat. No. 4,727.

Propagation:

(A) *Type cutting.*—Short tip cutting, with stems up to 2 cm.

(B) *Time to root.*—10 days at 21° C. in summer; 14 days at 21° C. in winter.

(C) *Rooting habit.*—Many very fine roots, fibrous.

Plant description:

(A) *Form.*—Intermediate, upright growth. Growing and scheduling practices can produce a small plant in a 10 cm pot up to a larger plant in a 15 cm and larger pot.

(B) *Habit of growth.*—Rate of growth moderate for this type of plant. Generally, shoots are formed at every node, with internodes being 12–25 mm. for a vegetative natural plant; height of plant above 10 cm. pot, approximately 25–25 cm. based on 2 to 3 applications of 3500 ppm B-9 SP growth regulator.

(C) *Foliage description.*—Leaves simple, opposite, slightly lobed. 1. Size: Average full grown leaf in a 10 cm flowering pot is 110 mm long×95 mm wide. 2. Shape: Ovate to elliptic, apex obtuse, base attenuate. 3. Texture: Glabrous, coriaceous, succulent. 4. Margin: Sinuate to crenate. 5. Color (mature foliage): Upper surface 147A; under surface 147B. Under certain conditions tips and margins of mature foliage on both upper and under surface are slightly streaked with 183A to 183C. 6. Durability: Excellent; no degradation observed even on the lower foliage of plants retained for months beyond normal life expectancy. 7. Foliar diseases: Resistant or immune to Powdery Mildew. Chlorosis, necrotic spots, tip die-back, stem rot and root rot have not been observed.

Flowering description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds (11–16 mm. in length) will continue for two months or more. Individual flowers last two weeks or more after opening. No perceived fragrance.

(B) *Flowering response.*—Flowering time under controlled daylength after start of short days is 9 weeks in summer to 11 weeks in winter.

(C) *Flowers borne.*—Compound dichasial cymes; peduncle length 5–13 cm., diameter 408 mm; pedicel length 5–7 mm, diameter greater than 1 mm.

(D) *Quantity of flowers.*—Very floriferous; floret count 80–100 per primary inflorescence, 400–500 total per 10 cm. pot plant, commercial culture.

(E) *Petals.*—1. Shape: Slightly pointed to almost round. 2. Color: Upper surface: 66C, maturing to 66D. Under surface: 51C to 51D, slightly streaked with 66D. 3. Number of petals: 4, united in corolla. 4. Flower diameter: 15 to 17 mm at maturity.

(F) *Reproductive organs.*—1. Stamens: 8 in number. a. Anther shape: Flat, elliptical, color yellow. b. Filament color: Light green. c. Pollen color: Yellow. 2. Pistils: a. Stigma shape: Flat, crystalline, color greenish white. b. Style color: Light green. c. Ovaries: 4-celled, color light green.

(G) *Flower diseases.*—None noted to date; resistant to Botrytis; no problems with color breaking or excess fading.

I claim:

1. A new and distinct Kalanchoe plant named Pink Glory, as described and illustrated.

* * * * *

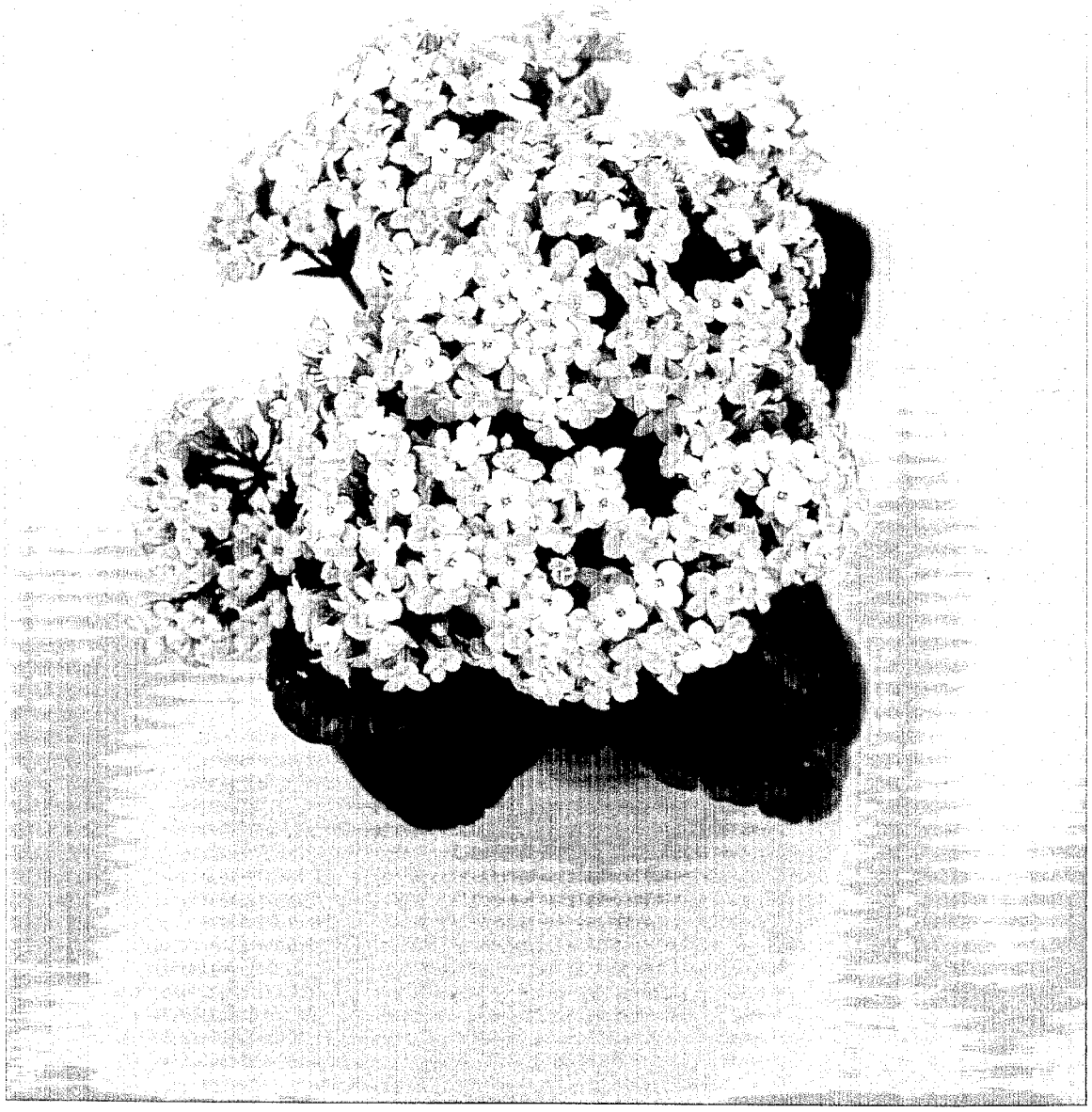

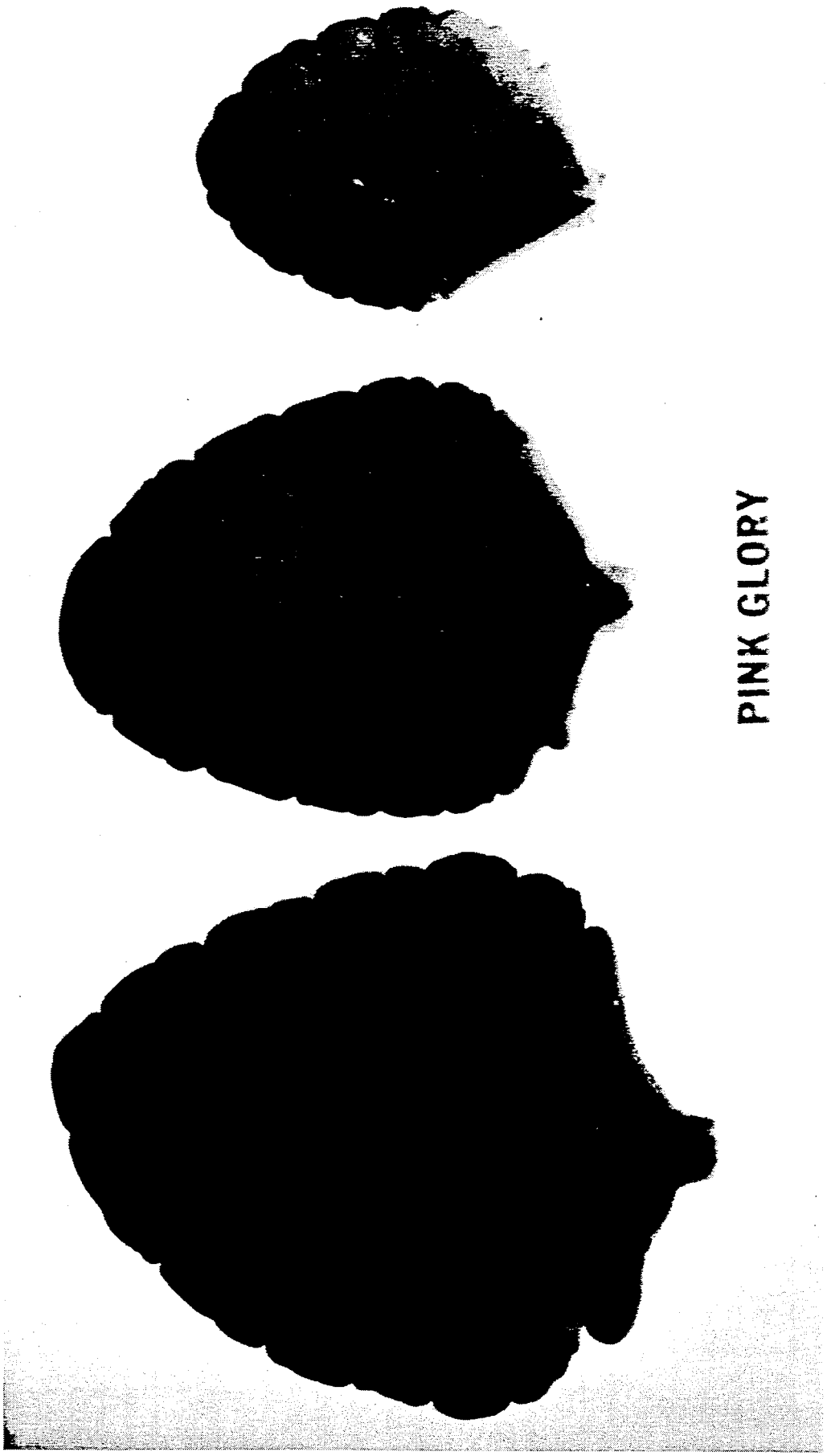
PINK GLORY